US010702313B1

(12) United States Patent
Horton

(10) Patent No.: US 10,702,313 B1
(45) Date of Patent: Jul. 7, 2020

(54) FACET BUTTRESS IMPLANT AND METHOD OF USING SAME

(71) Applicant: NuTech Spine, Inc., Birmingham, AL (US)

(72) Inventor: Kenneth L. Horton, Watersound, FL (US)

(73) Assignee: NuTech Spine, Inc., Birmingham, AL (US)

( * ) Notice: Subject to any disclaimer, the term of this patent is extended or adjusted under 35 U.S.C. 154(b) by 85 days.

(21) Appl. No.: 15/701,423

(22) Filed: Sep. 11, 2017

(51) Int. Cl.
| A61B 17/80 | (2006.01) |
| A61B 17/88 | (2006.01) |
| A61B 17/70 | (2006.01) |
| A61F 2/44 | (2006.01) |
| A61F 2/30 | (2006.01) |

(52) U.S. Cl.
CPC ........ *A61B 17/7059* (2013.01); *A61B 17/809* (2013.01); *A61F 2/44* (2013.01); *A61F 2002/30841* (2013.01)

(58) Field of Classification Search
CPC .............. A61B 17/707; A61B 17/7062; A61B 17/7064; A61B 17/7067–7068; A61B 17/809; A61B 17/7059; A61F 2/44; A61F 2002/30841
USPC .................... 606/70–71, 248, 279, 280–299; 623/17.11–17.16
See application file for complete search history.

(56) References Cited

U.S. PATENT DOCUMENTS

| 6,364,883 | B1* | 4/2002 | Santilli | A61B 17/7068 606/279 |
| 7,608,104 | B2* | 10/2009 | Yuan | A61B 17/1757 128/898 |
| 8,114,158 | B2* | 2/2012 | Carl | A61F 2/4405 606/247 |
| 8,845,697 | B2* | 9/2014 | Montello | A61B 17/701 606/280 |
| 8,926,665 | B2* | 1/2015 | Dennis | A61B 17/1671 606/247 |
| 2005/0143818 | A1* | 6/2005 | Yuan | A61B 17/1757 623/17.11 |
| 2005/0197700 | A1* | 9/2005 | Boehm, Jr. | A61F 2/4405 623/17.11 |
| 2006/0106381 | A1* | 5/2006 | Ferree | A61B 17/7014 606/248 |
| 2006/0241597 | A1* | 10/2006 | Mitchell | A61F 2/4684 606/247 |
| 2007/0016218 | A1* | 1/2007 | Winslow | A61B 17/025 606/99 |

(Continued)

*Primary Examiner* — Kevin T Truong
*Assistant Examiner* — Jessica Weiss
(74) *Attorney, Agent, or Firm* — C. Brandon Browning; Maynard, Cooper & Gale, PC

(57) ABSTRACT

A surgical implant for preventing withdrawal of a bone dowel graft from a facet joint, the apparatus including a plate having a posterior face and an anterior face, a passageway extending to and between the posterior face and the anterior face, an opening through the posterior face that is configured for detachably coupling to an inserter and one or more anti-migration projections extending outwardly from the anterior face. In use, the plate is placed over a bone dowel seated in a facet joint and coupled to the superior process and the inferior process by inserting a screw through the passageway into the inferior process.

12 Claims, 4 Drawing Sheets

(56) References Cited

U.S. PATENT DOCUMENTS

| | | | |
|---|---|---|---|
| 2010/0036419 A1* | 2/2010 | Patel | A61B 17/7065 606/249 |
| 2011/0160772 A1* | 6/2011 | Arcenio | A61B 17/7053 606/248 |
| 2013/0041410 A1* | 2/2013 | Hestad | A61B 17/7032 606/263 |
| 2015/0182268 A1* | 7/2015 | Donner | A61B 17/8066 606/281 |

* cited by examiner

FACET BUTTRESS IMPLANT AND METHOD OF USING SAME

FIELD OF INVENTION

The present invention is directed to a surgical implant and, more particularly, a cervical buttress plate and method of using same for preventing migration of a dowel out from between the articular surfaces of a facet joint.

BACKGROUND OF INVENTION

The facet joints, (or zygapophysial joints, zygapophyseal, apophyseal, or Z-joints) are a set of synovial, plane joints between the articular processes of two adjacent vertebrae which help support the weight of the body and prevent excessive rotational motion of the spine. These joints are formed between adjacent vertebrae by bilateral protrusions of bone of one vertebra that intersect with respective bilateral protrusions of bone of the vertebra located above and the vertebra located below. In particular, the superior processes or prezygapophysis project upward from a lower vertebra, and their articular surfaces are directed more or less backward (oblique coronal plane). The inferior processes or postzygapophysis project downward from a higher vertebra, and their articular surfaces are directed more or less forward and outward.

In between each pair of facet joints lies a facet joint capsule composed of cartilage. If the cartilage wears away in the course of consistent motion, the facet joints can become a source of pain in areas ranging from the mid-back to upper-back, from the neck to the base of the spine, and even in the shoulders. This is referred to as facet joint arthritis or facet arthropathy.

A common and effective treatment for facet joint pain is facet joint fusion. This procedure involves removal of the joint cartilage or drilling a passageway through the joint and placement of a spacer into the joint or passageway in order to restrict the joint's movement and thereby cause bone fusion across the joint. Often, the spacer will take the form of a natural or synthetic bone dowel or bone graft that is inserted into the facet joint. The use of bone dowels presents advantages over metal implants such as screws, which are typically inserted transversely through the intersecting facet joint bone protrusions. Advantages include a more efficacious bone fusion and permanent fixation once fusion is achieved.

Implantation of bone dowels between facet joints can be conducted using a minimally invasive procedure which takes place entirely through one or more cannulas inserted through a small incision in a patient's skin and muscle to provide direct access to the joint. Exemplary minimally invasive facet fusion procedures are described in U.S. Pat. Nos. 8,021,392 and 8,231,661. Alternatively, the procedure can be an open procedure.

Although use of bone dowels for affecting facet joint fusion and stabilization often succeeds, in some instances, dowels will migrate out of the drilled passages before fusion can be achieved. This most often occurs if the walls of the passage formed through the joint capsule or joint are smooth or if the dowel fails to include anti-migration features such as fins or ribs. Accordingly, there is a need for preventing the undesired, posterior migration of dowels from facet joints.

BRIEF SUMMARY OF THE INVENTION

The present invention is directed to an apparatus and method for preventing withdrawal of a bone dowel graft from a facet joint. According to one aspect of the invention, there is provided a surgical implant including a plate having a posterior face and an anterior face, a passageway extending to and between the posterior face and the anterior face, an opening through the posterior face that is configured for detachably coupling to an inserter and one or more anti-migration projections extending outwardly from the anterior face. The anti-migration projections are provided as a knurled surface located on a lateral portion of the anterior face and at least one tooth located on a medial portion of the anterior face. In one embodiment, the opening extends through the anterior surface of the plate and the knurled surface. In another embodiment, anti-migration projections include four teeth spaced equidistantly apart and around the passageway.

The plate is substantially rectangular and includes a medial end, a lateral end and a length extending to and between the medial end and the lateral end. The length is configured to extend across a facet joint and provide sufficient plate surface area to allow for secure attachment of the plate directly to the superior and inferior processes of the facet joint without protruding laterally beyond the superior process. The plate length may range between 0.375 inch and 0.6 inch, between 0.465 inch and 0.5 inch and between 0.470 inch and 0.485 inch. The plate also includes a cranial side, a caudal side and a width extending to and between the cranial side and the caudal side, the cranial and caudal sides alternating depending upon whether the plate is placed on the left or right side facet joint. The width of the plate is sufficient to cover a bone dowel located between the articular surfaces of the facet joint without protruding cranially or caudally beyond the superior and inferior processes. The plate width may range between 0.15 inch and 0.275 inch, between 0.190 inch and 0.225 inch and between 0.185 inch and 0.210 inch.

The opening in the posterior face of the plate has a medial edge located about halfway between the medial and lateral ends of the plate and a center located about 0.185 inch to 0.225 inch from the lateral end of the plate. The opening may extend partially of fully through the face. Similar to the opening, the passageway defines a second opening through the posterior face of the plate that has a lateral edge that is located about halfway between the medial and lateral sides of the plate. The second opening has a center that is located about 0.325 inch and 0.360 inch from the lateral end. The passageway also includes a posterior portion configured for receiving a screw head of a bone screw and an anterior portion having a diameter less than that of the screw head so that the screw may not pass completely through the passageway.

According to another aspect of the invention, there is provided a surgical kit for fusing or stabilizing a facet joint. The kit includes a plate including a posterior face and an anterior face, a passageway extending to and between the posterior face and the anterior face, an opening through the posterior face and one or more anti-slip projections extending outwardly from the anterior face. A bone planer is provided for imparting a flat, smooth surface to the superior and inferior processes and across the joint for receiving the plate. An inserter is provided for detachably coupling to the plate and arranging the plate over and across the facet joint. A self-tapping bone screw is provided for insertion through the passageway and into the inferior process. A screw driver is provided for rotating the screw and driving the screw into the superior process. When the joint fusing or stabilization procedure is to be carried out using a minimally invasive or mini-open procedure, the kit can include cannula for providing an approach to the facet joint through which the plate, planer, screw, inserter and screw driver may all pass. In one embodiment, the components of the kit are sterile and contained within sterile packaging such as a sterile tray or pouch.

According to yet another aspect of the invention, there is provided a method for preventing migration of a fixation member from between articular surfaces of a superior process of a lower vertebra and an inferior process of a higher vertebra. The method includes placing a plate over the fixation member and coupling the plate to the superior process and the inferior process. In particular, the method includes detachably coupling an inserter to the plate, followed by, inserting the plate through a cannula, followed by, placing the plate over the fixation member, followed by, detaching the inserter from the plate, followed by, inserting a screw through the plate and into the inferior process. In one embodiment, the method includes preparing the surgical site by removing bone from the superior process and the inferior process to provide a flat surface to which the plate is coupled. In another embodiment, the method includes coupling the plate to the inferior process by inserting a bone screw through a passageway of the plate and into the inferior process without inserting a screw into the superior process. In this embodiment, the plate is coupled to the superior process by impinging one or more teeth or a roughened or knurled surface extending from an anterior face of the plate into or onto the superior process.

BRIEF DESCRIPTION OF DRAWINGS

The disclosure can be better understood with reference to the following drawings. The elements of the drawings are not necessarily to scale relative to each other, emphasis instead being placed upon clearly illustrating the principles of the disclosure. Further, like reference numerals designate corresponding parts throughout the several views.

DETAILED DESCRIPTION OF THE INVENTION

Figure 6:
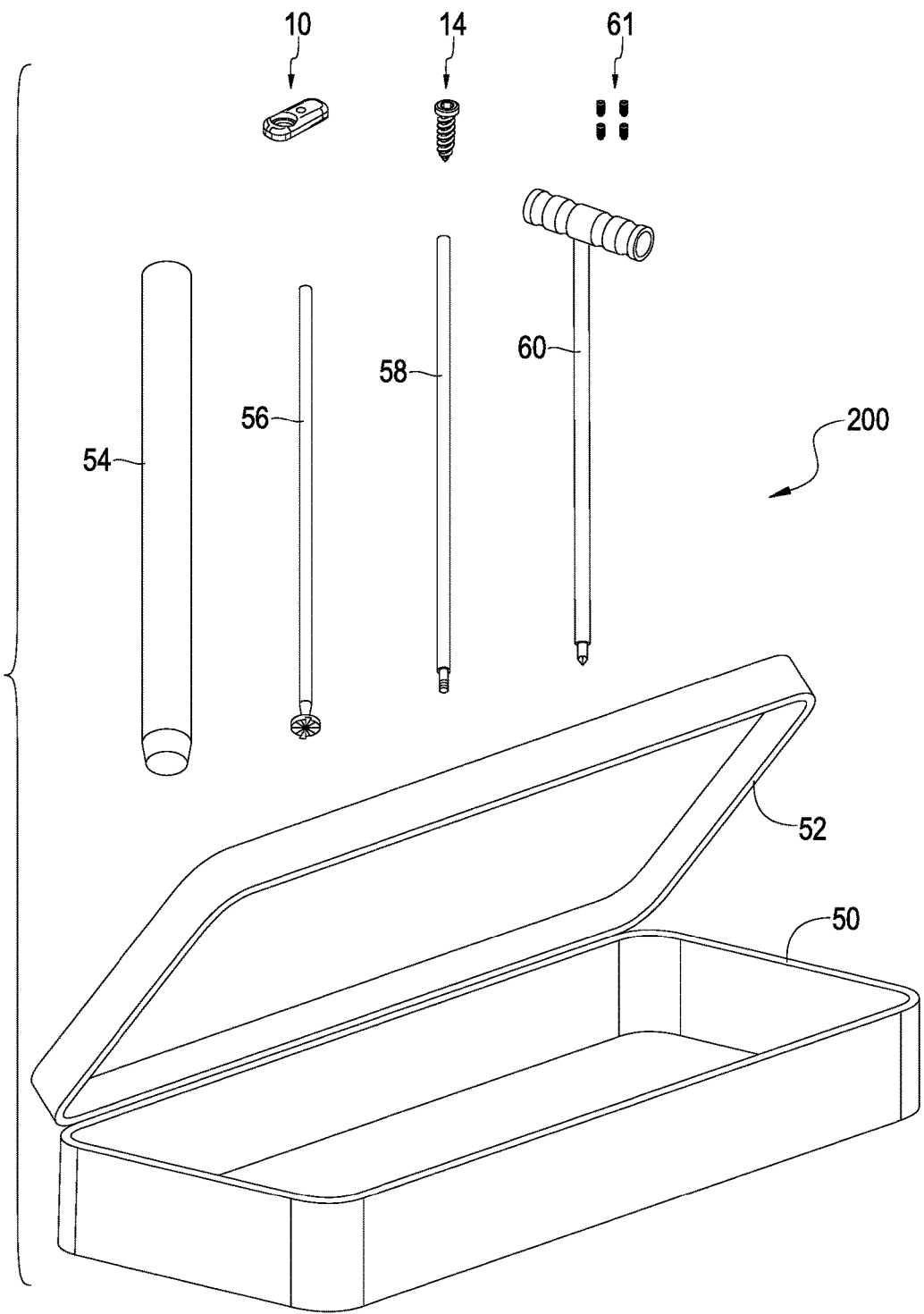
FIG. 6 is an exploded perspective view of a surgical kit in accordance with the present invention showing the surgical implant of FIG. 1, a cannula, a bone planer, an inserter, a bone screw, a screw driver and a sterile tray.
Figure 7:
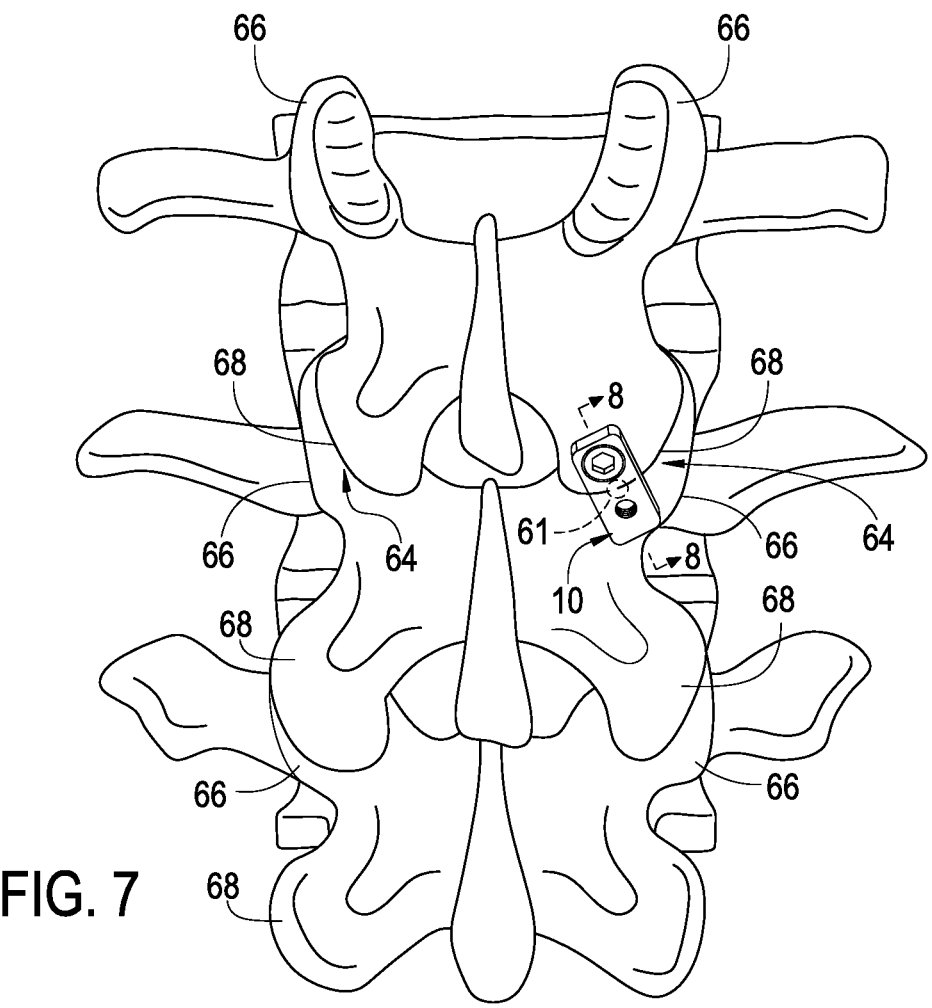
FIG. 7 is a perspective view of a facet joint showing the surgical implant of FIG. 1 coupled thereto and arranged to prevent migration of a bone dowel from the facet joint in accordance with the present invention.
Figure 8:
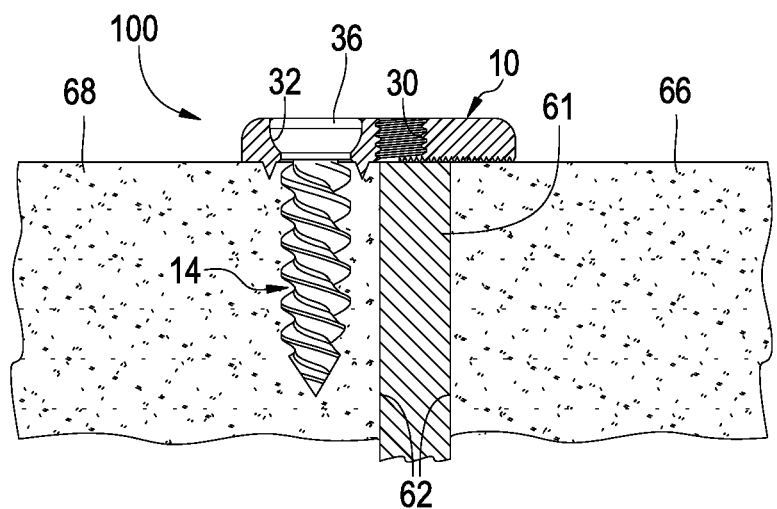
FIG. 8 is a sectional view of the facet joint of FIG. 7 along line 8-8.

FIGS. 1 through 5 illustrate a surgical implant 100 in accordance with the present invention. Surgical implant 100 is adapted and arranged for preventing the migration of a bone dowel out from between the articular surfaces of a joint. FIG. 6 illustrates a surgical kit 200 containing surgical implant 100 for use in conjunction with a minimally invasive or mini-open facet fusion surgical procedures. FIGS. 7 and 8 illustrate surgical implant 100 operatively coupled to vertebrae and arranged to prevent migration of a dowel out from between a superior process of a lower vertebra and an inferior process of a higher vertebra.

Figure 1:
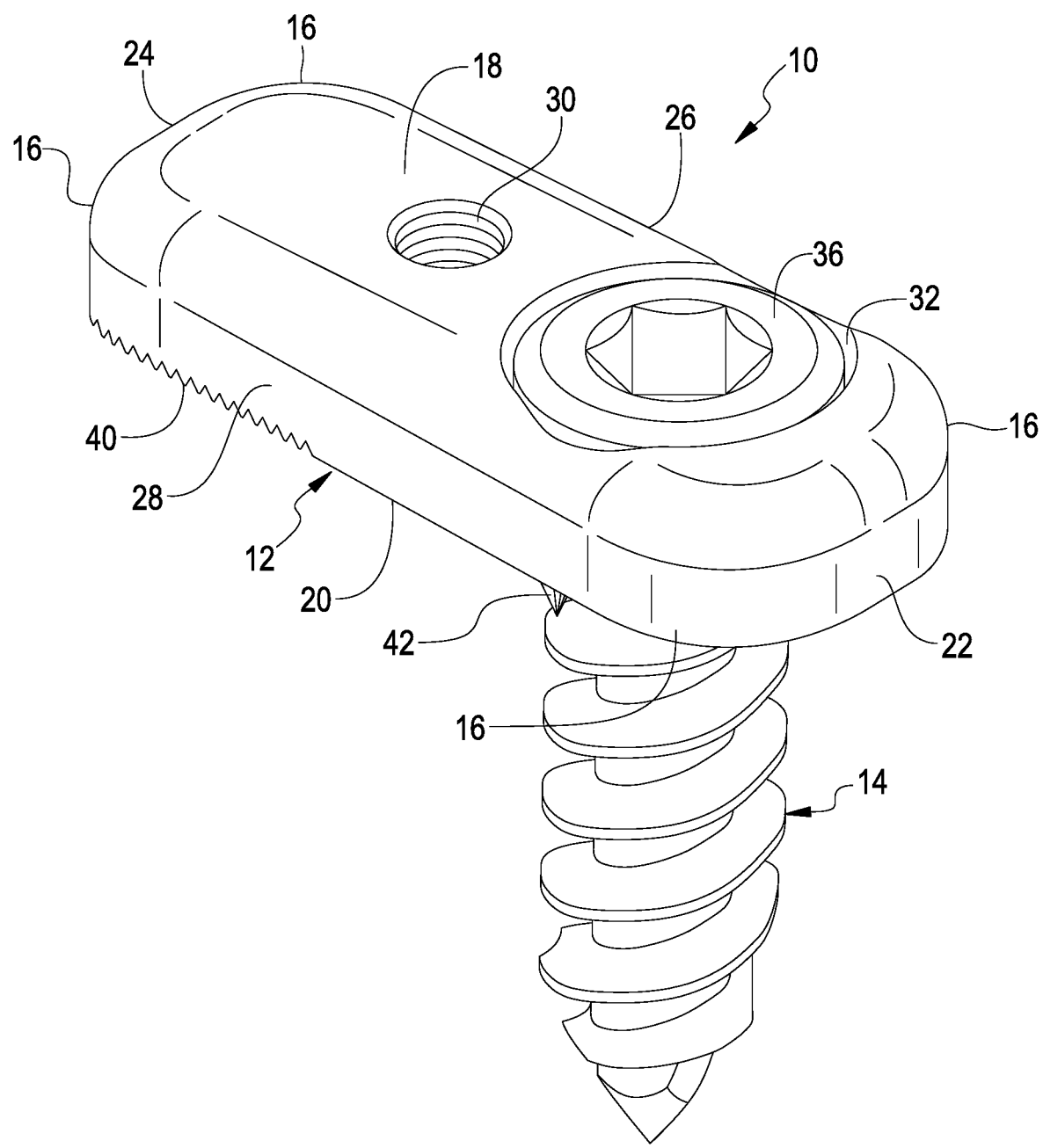
FIG. 1 is a perspective view of surgical implant in accordance with the present invention.
Figure 2:
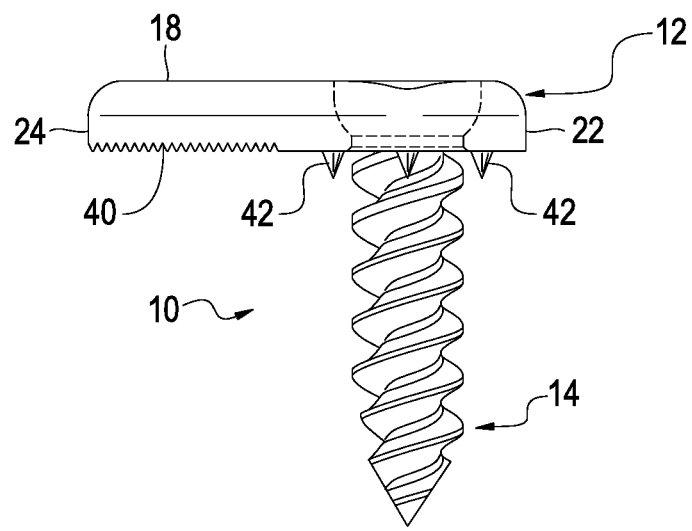
FIG. 2 is an elevational view of the surgical implant of FIG. 1.

Referring to FIG. 1, surgical implant 100 is composed of a metal plate 12 and a metal, self-tapping bone screw 14 having a length of about 0.472 inch. Plate 10 is fabricated from a biocompatible material such as titanium, stainless steel, cobalt-chrome alloys or tantalum. When fabricated from titanium, plate 10 may have a finish achieved by anodizing the titanium to medium green. Plate 12 is generally rectangular with rounded corners 16 and defined by a posterior face 18, an anterior face 20, a medial side 22, a lateral side 24, a cranial side 26 and a caudal side 28. Each rounded corner 16 has a radius of about 0.080 inch. Posterior face 18 is smooth with a substantially flat, centrally-located elongate portion and a periphery that surrounds the centrally-located elongate portion. The periphery transitions to and intersects with sides 22, 24, 26 and 28 along a continuous curved surface having a radius of about 0.039 inch. Contrary to the intersection of posterior face 18 with sides 22, 24, 26 and 28, anterior face 20 intersects with sides 22, 24, 26 and 28 to form a distinct, continuous edge at an angle of about 90° thereabout. Plate 10 has length extending between medial side 22 and lateral side 24 of about 0.472 inch and a width extending between cranial side 26 and caudal side 28 of about 0.197 inch, the cranial and caudal sides alternating depending upon whether the plate is placed on the left or right side facet joint.

Referring to FIGS. 1 through 5, plate 10 includes an opening 30 and a passageway 32. Opening 30 includes a threaded sidewall and is adapted for receiving an end of an implant inserter. Opening 30 may extend entirely or partially through plate 10. Opening 30 has a medial edge located about halfway between the medial and lateral ends of the plate and a center located about 0.197 inch from lateral side 24 of plate 10. Passageway 32 is configured for receiving bone screw 12. Passageway 32 includes a posterior portion 34 for containing a screw head 36 of screw 14 flush with posterior face 18 and an anterior portion 38 having a diameter that is less than that of the screw head so to prevent passage of the screw head completely through passage 32. Passageway 32 forms a second opening 34 through posterior face 18 having a center that is located about 0.344 inch from lateral side 24.

Figure 3:
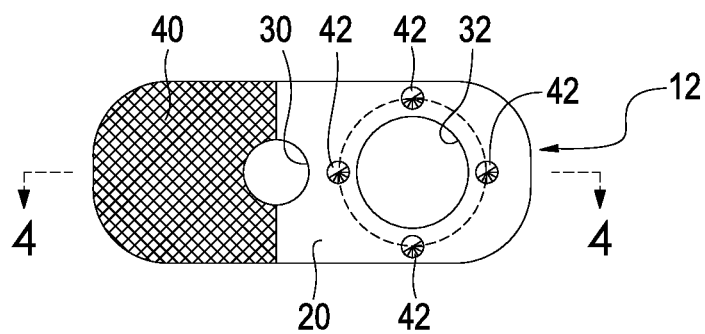
FIG. 3 is a plan view of a bottom of the surgical implant of FIG. 1.
Figure 4:
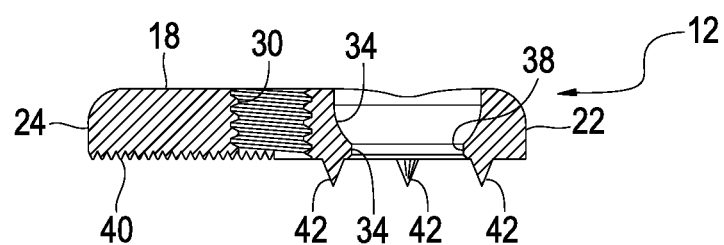
FIG. 4 is a sectional view of the surgical implant of FIG. 3 along line 4-4.
Figure 5:
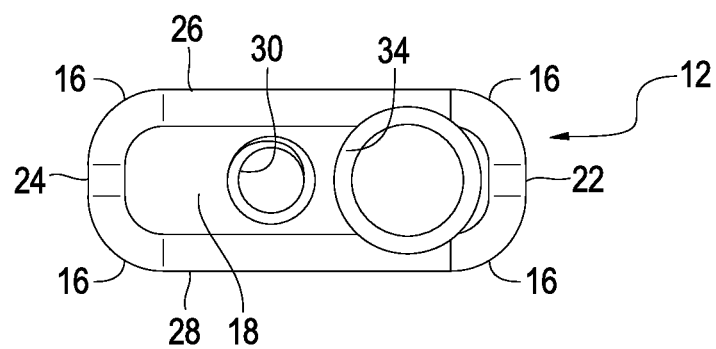
FIG. 5 is a top plan view of the surgical implant of FIG. 1.

Referring to FIG. 3, anterior face 20 includes a roughened or knurled finish 40 for assisting with fixation of plate 10 to bone. Knurled finish 40 covers an area bounded by lateral side 24, cranial side 26, caudal side 28 and a line extending between sides 26 and 28 and through a center of opening 30. Preferably, knurled finish 40 is a 0.20 inch knurl in a diamond pattern with a depth of about 0.008 inch. The remainder of anterior face 20 of plate 10 is substantially smooth, except for the passage therethrough of passageway 32 and four, acutely pointed teeth 42. Teeth 42 are provided as right circular cones with lines originating from the apex and intersecting anterior face 20 at a 45 degree angle. In a particular embodiment of the invention, teeth 42 are arranged equidistantly apart around passageway 32 thereby defining a circle concentric with the passageway with a diameter 0.003 inch greater than that of the passageway where it exits through anterior face 20. It is contemplated that there may be additional teeth.

Surgical kit 200 is illustrated in FIG. 6. Surgical kit 200 is shown as a rectangular, plastic or metal tray 50 including a closed bottom, a continuous sidewall extending upwardly from a periphery of the closed bottom and a removable lid 52 adhered to a rim formed by the continuous sidewall. Lid 52 hermetically seals the contents of tray therein. Contained within tray 50 are a number of sterilized instruments required to place and fix surgical implant 100 at a desired site within the body. In particular, tray 50 includes plate 10, bone screw 14, a guide cannula 54 for providing access through an incision to a joint, a bone planer 56 for flattening and preparing bone surfaces, an inserter 58 for inserting plate 10 through the guide cannula and a screw driver 60 for fixing the bone screw to plate 10 and bone. Each of tray 50, bone screw 14, cannula 54, bone planer 56, inserter 58 and screw driver 60 are known in the art and may be one of several known designs. It is contemplated that surgical kit 200 may also include facet fusion devices and instruments required for accessing a facet joint and placing a fusion dowel between the articular surfaces of the joint. Thus, for example, surgical kit may include one or more allograft bone dowels for insertion into the joint, a drill bit for drilling a hole between the articular surfaces of the facet joint, guide pins for locating the facet joint, drill guides for guiding the drill bit to the joint, expansion cannulas for progressively enlarging the approach to the joint through a minimally invasive incision and a dowel inserter for inserting the dowel into the joint through a cannula.

Surgical kit 200 can be used in a facet joint surgical procedure. A particular embodiment of this invention can be used in a cervical facet joint surgical procedure and another embodiment can be used on a lumbar facet joint surgical procedure. More particularly, surgical implant 100 is used for preventing migration of a fixation member from between articular surfaces of a superior process of a lower vertebra and an inferior process of a higher vertebra. Referring to FIGS. 7 and 8, the method includes placing plate 10 over a bone dowel 61 that is located between articular surfaces 62 of a facet joint 64 and coupling the plate to a superior process 66 and a inferior process 68. To begin, facet joint 64 is approached through guide cannula 54 which inserted through an incision. Planer 56 is inserted through the cannula and a tip of the planer is inserted a short distance into the joint. The tip of the planer functions to properly locate the planer relative to the joint and superior process 66 and the inferior process 68. With planer 56 properly positioned, the planer is rotated so that cutting edges of the planer cut away bone of superior process 66 and the inferior process 68. Once a flat surface 70 is formed across the joint, planer 56 is removed from cannula 54.

With the surfaces of superior process 66 and the inferior process 68 flattened, bone dowel is 61 is placed within the joint using means well known in the art. Thereafter, a threaded tip of inserter 58 is inserted into opening 30 thereby securing plate 10 to inserter 58. Using the inserter, plate 10 is advanced through cannula 54 and placed over facet joint 64 with passageway 32 located over inferior process 68 and knurled surface 40 located over superior process 66. Plate 10 is then pressed against superior process 66 and the inferior process 68 with force sufficient to cause teeth 42 is penetrate into inferior process 68. Likewise, knurled surface 40 is caused to impinge upon superior process 66. With plate 10 fixed against superior process 66 and the inferior process 68, inserter 58 is rotated, detached from plate 10 and removed from cannula 54.

With plate 10 in place over the joint, screw 14 is operatively engaged with a tip of screw driver 60, and screw 14 is inserted through cannula 54 and into passageway 32. While placing a slight downward force on screw driver 60, the screw driver is rotated causing screw 14 is drive into the bone of inferior process 68. Once screw head 36 of screw 14 is flush with posterior face 18 of plate 10, rotation of screw driver is terminated, and the screw driver is removed from cannula 54. At this point, plate 10 is securely fixed to superior process 66 and the inferior process 68 and arranged to prevent posterior migration of dowel 61 from between the articular surface of facet joint 61. Cannula 54 is then removed from the incision, and the incision closed.

As will be apparent to one skilled in the art, various modifications can be made within the scope of the aforesaid description. Such modifications being within the ability of one skilled in the art form a part of the present invention and are embraced by the claims below. For example, it is understood that the knurled anterior surface may extend across the entirety of the anterior surface or include teeth like those found encircling the passageway. Additionally, the surgical kit may include multiple surgical implants, for example, when a bilateral fusion is necessary. Further, it is contemplated that the surgical implant can be used to prevent undesired migration of dowels that are placed in parts of the body other than facet joints, such as dowels placed within sacroiliac joints.

What is claimed is:

1. A method for preventing migration of a fixation member from between articular surfaces of a superior process of a lower vertebra and an inferior process of a higher vertebra, the method comprising:
    detachably coupling a surgical implant inserter to a plate, followed by,
    inserting the plate through a cannula, followed by,
    placing the plate over a fixation member, followed by,
    detaching the surgical implant inserter from the plate, followed by,
    inserting a screw through the plate and into the inferior process, and
    coupling the plate to the superior process and the inferior process,
    wherein the plate includes a posterior face and an anterior face, a passageway extending to and between the posterior face and the anterior face, an opening through the posterior face that is configured for detachably coupling to the surgical implant inserter, the opening being spaced apart from the passageway, and one or more anti-migration projections extending outwardly from the anterior face, and
    wherein coupling the plate to the inferior process includes inserting the screw through the passageway of the plate and into the inferior process without inserting the screw into the superior process.

2. The method of claim 1 further including removing bone from the superior process and the inferior process to provide a flat surface and coupling the plate to the flat surface.

3. The method of claim 1 wherein coupling the plate to the superior process includes impinging the one or more anti-migration projections extending from the anterior face of the plate into the superior process.

4. The method of claim 1 further including detachably coupling the surgical implant inserter directly to the opening.

5. The method of claim 1 wherein the one or more anti-migration projections include a knurled surface located on a lateral portion of the anterior face and at least one tooth located on a medial portion of the anterior face.

6. The method of claim 5 wherein the opening extends at least partially through the knurled surface.

7. The method of claim 1 further including removing the plate and the screw from a sterile packaging.

8. The method of claim 1 further including removing the plate, the cannula and the screw from a sterile packaging.

9. The method of claim 1 wherein the plate further includes a medial end, a lateral end and a length extending to and between the medial end and the lateral end, the length being between 0.465 inch and 0.5 inch.

10. The method of claim 9 wherein the opening through the plate has a center located 0.185 inch to 0.225 inch from the lateral end.

11. The method of claim 9 wherein the plate further includes a cranial side, a caudal side and a width extending to and between the cranial side and the caudal side, the width being between 0.190 inch and 0.225 inch.

12. The method of claim 10 wherein the passageway through the plate has a center that is located 0.325 inch to 0.360 inch from the lateral end.

\* \* \* \* \*